United States Patent

Durette et al.

Patent Number: 5,821,261
Date of Patent: Oct. 13, 1998

[54] SUBSTITUTED SATURATED AZA HETEROCYCLES AS INHIBITORS OF NITRIC OXIDE SYNTHASE

[75] Inventors: Philippe L. Durette, New Providence; Thomas Lanza, Jr., Edison, both of N.J.

[73] Assignee: Merck & Co., Inc., Rahway, N.J.

[21] Appl. No.: 745,355

[22] Filed: Nov. 8, 1996

Related U.S. Application Data

[60] Provisional application No. 60/008,390 Feb. 27, 1995.

[51] Int. Cl.$^6$ .......................... C07D 211/06; A01N 43/40
[52] U.S. Cl. .......................... 514/428; 514/408; 514/315; 548/570; 546/246; 544/242
[58] Field of Search ................. 514/408, 428, 514/315; 548/570; 546/246; 544/242

[56] References Cited

U.S. PATENT DOCUMENTS 5,252,586 10/1993 Cain et al. ............................. 514/317
5,489,603 2/1996 Uneme et al. .......................... 514/365

OTHER PUBLICATIONS

Webb et al. J. Org. Chem., vol. 56, No. 9, 1991, 3009–3016.
Nakane, et al., FEBS Letters, 316, 175–182 (1993).
Marsden, et al FEBS Letters, 307, 287–293 (1992).
Geller, et al, PNAS, 90, 34915 (1993).
Moncada, et al., Pharmacol, Reviews, 43, 109–142 (1991).
Nathan, FASEB J., 6, 3051–64 (1992).
Wright, et al., Card, Res., 26, 48–57 (1992).
Kilbourn, et al., PNAS, 87, 3628–32 (1990).
Beasley and Brunner, Kidney, Int., 42, Suppl., 38, S96–S100 (1992).
Hibbs, et al., J. Clin. Invest., 89, 867–77 (1992).
Miller, et al., J. Pharmacol. Exp. Ther., 264, 11–16 (1990).
Ialenti, et al., Br. J. Pharmacol., 110, 701–6 (1993).
Stevanovic–Racic, et al., Arth. & Rheum, 37, 1062–9 (1994).
Huang, et al., Science, 265, 1883–5 (1994).
J. Org. Chem., 1991, 56(9): 3010–3016.

*Primary Examiner*—Mukund J. Shah
*Assistant Examiner*—Pavanaram K. Sripada
*Attorney, Agent, or Firm*—Mollie M. Yang; David L. Rose

[57] ABSTRACT

Disclosed herein are compounds of Formula (I)

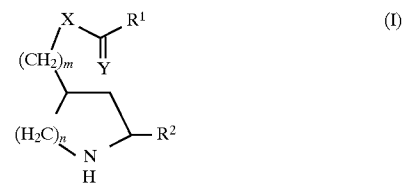

and pharmaceutically acceptable salts thereof which have been found useful in the treatment of nitric oxide synthase mediated diseases and disorders, including neurodegenerative disorders, disorders of gastrointestinal motility and inflammation. These disease and disorders include hypotension, septic shock, toxic shock syndrom, hemodialysis, IL-2 therapy such as in cancer patients, cachexia, immnunosuppression such as in transplant therapy, autoimmune and/or inflammatory indications including sunburn or psoriasis and respiratory conditions such as bronchitis, asthma, and acure respiratory distress (ARDS), myocarditis, heart failure, atherosclerosis, arthritis, rheumatoid arthritis, chronic or inflammatory bowel disease, ulcerative colitis, Crohn's disease, systemic lupus erythematosis (SLE), ocular conditions such as ocular hypertension and uveitis, type 1 diabetes, insulin-dependent diabetes mellitus and cystic fibrosis. Compounds of Formula I are also useful in the treatment of hypoxia, hyperbaric oxygen convulsions and toxicity, dementia, Sydenham's chorea, Parkinson's disease, Huntington's disease, amyotrophic lateral sclerosis, multiple sclerosis, Korsakoffs disease, imbecility related to cerebral vessel disorder, ischemic brain edema, sleeping disorders, schizophrenia, depression, PMS, anxiety, drug addiction, pain, migraine, immune complex disease, as immunosupressive agents and for preventing or reversing tolerance to opiates and diazepines.

7 Claims, No Drawings

SUBSTITUTED SATURATED AZA HETEROCYCLES AS INHIBITORS OF NITRIC OXIDE SYNTHASE

CROSS REFERENCE TO RELATED APPLICATION

The present invention is based on, and claims priority from 60/008,390, filed Dec. 8, 1995.

BACKGROUND OF THE INVENTION

This application is directed to inhibitors of nitric oxide synthase, and in particular substituted azacycle derivatives.

Nitric Oxide in Biology

The emergence of nitric oxide (NO), a reactive inorganic radical gas, as a molecule contributing to important physiological and pathological processes is one of the major biological revelations of recent times. This molecule is produced under a variety of physiological and pathological conditions by cells mediating vital biological functions. Examples include endothelial cells lining the blood vessels. Nitric oxide derived from these cells relaxes smooth muscle and regulates blood pressure and has significant effects on the function of circulating blood cells such as platelets and neutrophils as well as on smooth muscle, both of the blood vessels and also of other organs such as the airways. In the brain and elsewhere nitric oxide serves as a neurotransmitter in non-adrenergic non-cholinergic neurons. In these instances nitric oxide appears to be produced in small amounts on an intermittent basis in response to various endogenous molecular signals. In the immune system nitric oxide can be synthesized in much larger amounts on a protracted basis. Its production is induced by exogenous or endogenous inflammatory stimuli, notably endotoxin and cytokines elaborated by cells of the host defense system in response to infectious and inflammatory stimuli. This induced production results in prolonged nitric oxide release which contributes both to host defense processes such as the killing of bacteria and viruses, as well as pathology associated with acute and chronic inflammation in a wide variety of diseases. The discovery that nitric oxide production is mediated by a unique series of three closely related enzymes, named nitric oxide synthases, which utilize the amino acid arginine and molecular oxygen as co-substrates, has provided an understanding of the biochemistry of this molecule and provides distinct pharmacological targets for the inhibition of the synthesis of this mediator, which should provide significant beneficial effects in a wide variety of diseases.

Nitric Oxide Synthases

Nitric oxide and L-citrulline are formed from L-arginine via the dioxygenase activity of specific nitric oxide synthases (NOSs) in mammalian cells. In this reaction, L-arginine, $O_2$ and NADPH are co-substrates while FMN, FAD and tetrahydrobiopterin are co-factors. NOSs fall into two distinct classes, constitutive NOS (cNOS) and inducible NOS (iNOS). Two constitutive NOSs have been identified. They are:

(i) a constitutive, $Ca^{++}$/calmodulin dependent enzyme, located in the endothelium (ecNOS or NOS 3), that releases NO in response to receptor or physical stimulation;

(ii) a constitutive, $Ca^{++}$/calmodulin dependent enzyme, located in the brain (ncNOS or NOS 1) and elsewhere, that releases NO in response to receptor or physical stimulation.

The third isoform identified is inducible NOS (iNOS or NOS 2):

(iii) a $Ca^{++}$ independent enzyme which is induced after activation of vascular smooth muscle, macrophages, endothelial cells, and a large number of other cells by endotoxin and cytokines. Once expressed, this inducible NO synthase produces NO in relatively large amounts for long periods of time.

Spectral studies of both the mouse macrophage INOS and rat brain ncNOS have shown that these enzymes (which have been classified as P-450-like enzymes from their CO-difference spectra) contain a heme moiety. The structural similarity between NOS and the P-450-flavoprotein complex suggests that the NOS reaction mechanism may be similar to P-450 hydroxylation and/or peroxidation. This indicates that NOS belongs to a class of flavohemeproteins which contain both heme and flavin binding regions within a single protein in contrast to the multiprotein NADPH oxidase or Cytochrome P-450/NADPH Cyt c reductase complexes.

Distinct Functions of NO Produced by Different Nitric Oxide Synthases

The NO released by the constitutive enzymes (NOS 1 and NOS 3) acts as an autocoid mediating a number of physiological responses. Two distinct cDNAs accounting for the activity of NOS 1 and NOS 3 in man have been cloned, one for NOS 1 (Nakane et al., *FEBS Letters*, 316, 175–182, 1993) which is present in the brain and a number of peripheral tissues, the other for an enzyme present in endothelium (NOS 3) (Marsden et al., *FEBS Letters*, 307, 287–293, 1992). This latter enzyme is critical for production of NO to maintain vasorelaxation. A second class of enzyme, iNOS or NOS 2, has been cloned from human liver (Geller et al., *PNAS*, 90, 3491–5, 1993), and identified in more than a dozen other cells and tissues, including smooth muscle cells, chondrocytes, the kidney and airways. As with its counterpart from the murine macrophage, this enzyme is induced upon exposure to cytokines such as gamma interferon (IFN-γ), interleukin-1β (IL-1β), tumor necrosis factor (TNF-α) and LPS (lipopolysaccharide). Once induced, iNOS expression continues over a prolonged period of time. The enzyme does not require exogenous calmodulin for activity.

Endothelium derived relaxation factor (EDRF) has been shown to be produced by NOS 3 (Moncada et al., *Pharmacol. Reviews*, 43, 109–142, 1991). Studies with substrate analog inhibitors of NOS have shown a role for NO in regulating blood pressure in animals and blood flow in man, a function attributed to NOS 3. NO has also been shown to be an effector of the cytotoxic effects of activated macrophages (Nathan, *FASEB J.*, 6, 3051–64, 1992) for fighting tumour cells and invading microorganisms (Wright et al., *Card. Res.*, 26,48–57, 1992 and Moncada et al., *Pharmacological Review*, 43, 109–142, 1991). It also appears that the adverse effects of excess NO production, in particular pathological vasodilation and tissue damage, may result largely from the effects of NO synthesized by the NOS 2.

NO generated by NOS 2 has been implicated in the pathogenesis of inflammatory diseases. In experimental animals, hypotension induced by LPS or TNF-α can be reversed by NOS inhibitors and reinitiated by L-arginine (Kilbourn et al., *PNAS*, 87, 3629–32, 1990). Conditions which lead to cytokine-induced hypotension include septic shock, hemodialysis (Beasley and Brenner, *Kidney Int.*, 42, Suppl., 38, S96–S100, 1992) and IL-2 therapy in cancer patients (Hibbs et al., *J. Clin. Invest.*, 89, 867–77, 1992). NOS 2 is implicated in these responses, and thus the possibility exists that a NOS inhibitor would be effective in ameliorating cytokine-induced hypotension. Recent studies in animal models have suggested a role for NO in the pathogenesis of inflammation and pain, and NOS inhibitors have been shown to have beneficial effects on some aspects of the inflammation and tissue changes seen in models of inflammatory bowel disease, (Miller et al., *J. Pharmacol. Exp. Ther.*, 264, 11–16, 1990), cerebral ischemia, and arthritis (Ialenti et al., *Br. J. Pharmacol.*, 110, 701–6, 1993; Stevanovic-Racic et al., *Arth. & Rheum.*, 37, 1062–9, 1994). Moreover, transgenic mice deficient in NOS 1 show diminished cerebral ischemia (Huang et al., *Science*, 265, 1883–5, 1994).

Further conditions where there is an advantage in inhibiting NO production from L-arginine include therapy with cytokines such as TNF, IL-1 and IL-2 or therapy with cytokine-inducing agents, for example, 5,6-dimethylxanthenone acetic acid, and as an adjuvant to short term immunosuppression in transplant therapy. In addition, compounds which inhibit NO synthesis may be of use in reducing the NO concentration in patients suffering from inflammatory conditions in which an excess of NO contributes to the pathophysiology of the condition, for example, adult respiratory distress syndrome (ARDS) and myocarditis.

There is also evidence that an NO synthase enzyme may be involved in the degeneration of cartilage which takes place in autoimmune and/or inflammatory conditions such as arthritis, rheumatoid arthritis, chronic bowel disease and systemic lupus erythematosis (SLE). It is also thought that an NO synthase enzyme may be involved in insulin-dependent diabetes mellitus. Therefore, a yet further aspect of the present invention provides compounds of formula I or salts thereof in the manufacture of a medicament for use in cytokine or cytokine-inducing therapy, as an adjuvant to short term immunosuppression in transplant therapy, for the treatment of patients suffering from inflammatory conditions in which an excess of NO contributes to the pathophysiology of the condition.

Webb and Eigenbrot (*J. Org. Chem.*, 1991, 56(9):3010–3016) report the synthesis of conformationally restricted arginine analogs having the formula

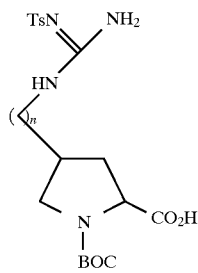

where n is 0 or 1, Ts is toluenesulfonyl, and BOC is tert-butoxycarbonyl. For the compound where n is 1, the Ts and BOC protecting groups are removed to provide 4-guanidinomethyl-prolines. These arginine analogs are intended to be introduced into peptides, and no biological activity therefor is disclosed.

SUMMARY OF THE INVENTION

The invention disclosed herein encompasses compounds of Formula (I)

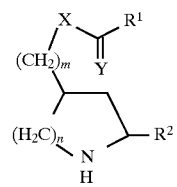

and pharmaceutically acceptable salts thereof which have been found to be useful in the treatment of nitric oxide synthase-mediated diseases and disorders, including neurodegenerative disorders, disorders of gastrointestinal motility and inflammation. These diseases and disorders include hypotension, septic shock, toxic shock syndrome, hemodialysis, IL-2 therapy such as in cancer patients, cachexia, immunosuppression such as in transplant therapy, autoimmune and/or inflammatory indications including sunburn, eczema or psoriasis and respiratory conditions such as bronchitis, asthma, oxidant-induced lung injury and acute respiratory distress (ARDS), glomerulonephritis, inflammatory sequelae of viral infections, myocarditis, heart failure, atherosclerosis, arthritis, rheumatoid arthritis, chronic or inflammatory bowel disease, ulcerative colitis, Crohn's disease, systemic lupus erythematosis (SLE), ocular conditions such as ocular hypertension, retinitis and uveitis, type 1 diabetes, insulin-dependent diabetes mellitus and cystic fibrosis. Compounds of Formula I are also useful in the treatment of hypoxia, hyperbaric oxygen convulsions and toxicity, dementia, Sydenham's chorea, Parkinson's disease, Huntington's disease, amyotrophic lateral sclerosis, multiple sclerosis, Korsakoff's disease, imbecility related to cerebral vessel disorder, NO mediated cerebral trauma and related sequelae, ischemic brain edema, sleeping disorders, schizophrenia, depression, pre-menstrual syndrome (PMS), anxiety, drug addiction, pain, migraine, immune complex disease, as immunosuppressive agents, acute allograft rejection, infections caused by invasive microorganisms which produce NO, radiocontrast induced renal failure and for preventing or reversing tolerance to opiates and diazepines.

DETAILED DESCRIPTION OF THE INVENTION

The invention disclosed herein encompasses a method for inhibiting the activity of nitric oxide synthases comprising administering to a subject suffering from a nitric oxide synthase mediated disease a non-toxic therapeutically effective amount of a compound of Formula (I)

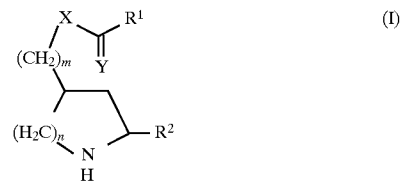

or a pharmaceutically acceptable salt thereof wherein:
m is 0, 1, 2 or 3;
n is 1 or 2;
$R_1$ is
 (1) —$SR_3$;
 (2) —$N(R_4)(R_5)$;
 (3) hydrogen,
 (4) $C_{1-6}$alkyl,
 (5) $C_{2-6}$alkenyl, (6) $C_{2-6}$alkynyl,
(7) $R_6$-A,
(8) 3- to 10-membered monocyclic ring which optionally contains 1 or 2 heteroatoms selected from S, O, and N, each of (4) to (8) being optionally mono- or di- substituted, the substituents being independently selected from
  (a) $R_8$, and
  (b) $C_{1-6}$alkyl, with the proviso that for items (4), (5) and (6) the substituent is other than $C_{1-6}$alkyl;

$R_2$ is —$COOR_9$;

$R_3$ is $R_7$ optionally substituted with $R_8$, $R_4$ and $R_5$ are each independently selected from the group consisting of
(1) hydrogen,
(2) hydroxy,
(3) amino,
(4) cyano,
(5) nitro,
(6) trifluoromethyl,
(7) $C_{1-6}$alkyl,
(8) $C_{2-6}$alkenyl,
(9) $C_{2-6}$alkynyl,
(10) $R_6$-A,
(11) 3- to 10-membered monocyclic ring which optionally contains 1 or 2 heteroatoms selected from S, O, and N,
(12) $R_7$-$C_{3-6}$cycloalkyl, each of (7) to (12) being optionally mono- or di- substituted, with substituents being independently selected from
  (a) R8, and
  (b) $C_{1-6}$alkyl, with the proviso that (7), (8) and (9) must each be other than $C_{1-6}$alkyl, or $R_4$, $R_5$ together with the nitrogen to which they are attached join to form a 4- to 6-membered saturated or unsaturated ring containing 1 or 2 heteroatoms selected from S, O and N;

R6 is
(1) a bond, or
(2) $R_7$, $R_7$ is
(1) $C_{1-6}$alkyl,
(2) $C_{2-6}$alkenyl, or
(3) $C_{2-6}$alkynyl, $R_8$ is
(1) hydroxy,
(2) $C_{1-6}$alkylcarbonyl,
(3) $C_{1-6}$alkoxy
(4) amino,
(5) mono- and di-$C_{1-6}$alkylamino,
(6) carboxyl,
(7) $C_{1-6}$alkylthio,
(8) $C_{1-6}$alkyl-$S(O)_k$—, where k is 1 or 2,
(9) $C_{1-6}$alkyoxycarbonyl,
(10) halo selected from fluoro, chloro, bromo, and iodo, and
(11) $CF_3$.

$R_9$ is H, $C_{1-6}$alkyl or phenyl-$C_{0-3}$alkyl,

A is
(1) phenyl
(2) naphthyl, or
(3) heteroaryl selected from the group consisting of
  (a) pyridyl,
  (b) pyrrolyl,
  (c) furanyl,
  (d) isothiazolyl,
  (e) imidazolyl,
  (f) benzimidazolyl,
  (g) tetrazolyl,
  (h) pyrazinyl,
  (i) pyrimidyl,
  (j) quinolyl,
  (k) isoquinolyl,
  (l) benzofuranyl,
  (m) isobenzofuryl,
  (n) benzothienyl,
  (o) pyrazolyl,
  (p) indolyl,
  (q) isoindolyl,
  (r) purinyl,
  (s) carbazolyl,
  (t) isoxazolyl,
  (u) thiazolyl,
  (v) triazolyl
  (w) oxazolyl,
  (x) oxadiazolyl,
  (y) thiadiazolyl
  (z) benzthiazolyl,
  (a') benzoxazolyl, and
  (b') thienyl, X is S or NH, Y is selected from the group consisting of
(1) O,
(2) S,
(3) —NH, and
(4) —N—$R_7$, wherein $R_7$ is optionally mono- or di-substituted, the substituents being independently selected from $R_8$;

with the proviso that at least two of the groups X, Y and $R_1$ are an amino or substituted amino group.

Within this embodiment there is a genus of compounds wherein $R_1$ is —$N(R_4)(R_5)$ Y is selected from the group consisting of
(1) —NH, or
(2) —N—$R_7$, and $R_4$, $R_5$, $R_7$ are as defined above.

Within this genus there is a class of compounds wherein
m is 0 or 1;
n is 1;
$R_1$ is —$N(R_4)(R_5)$,
$R_2$ is —$COOR_9$;
$R_9$ is H or $C_{1-3}$alkyl;
X is NH;
Y is NH; and
$R_4$ and $R_5$ are as defined above.

In another aspect of the present invention there are provided novel compounds of Formula (I) with the further proviso that when n is 1, X and Y are each —NH, and $R_1$ is —$NH_2$, m is other than 0 or 1.

Compounds useful for the method of the present invention include, but are not limited to:

(4S)-4-(guanidinomethyl)-L-proline dihydrochloride;
(4R)-4-(guanidinomethyl)-L-proline dihydrochloride;
(4S)-4-(guanidino)-L-proline dihydrochloride;
(4R)-4-(guanidino)-L-proline dihydrochloride;
(4S)-4-(isothioureidomethyl)-L-proline dihydrochloride; and
(4R)-4-(guanidinomethyl)-L-proline methyl ester dihydrochloride.

For purposes of this specification alkyl is defined to include linear, branched, and cyclic structures, with $C_{1-6}$alkyl including methyl, ethyl, propyl, 2-propyl, s- and t-butyl, butyl, pentyl, hexyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$ alkylthio is intended to include alkylthio groups of from 1 to 6 carbon atoms of a straight, branched or cyclic configuration. Examples of lower alkylthio groups include methylthio, propylthio, isopropylthio, cyclohexylthio, etc. By way of illustration, the propylthio group signifies $—SCH_2CH_2CH_3$.

Heteroaryl includes, but is not limited to, pyridyl, pyrrolyl, furanyl, thienyl, isothiazolyl, imidazolyl, benzimidazolyl, tetrazolyl, pyrazinyl, pyrimidyl, quinolyl, isoquinolyl, benzofuranyl, isobenzofuryl, benzothienyl, pyrazolyl, pyridazinyl, indolyl, isoindolyl, purinyl, carboxazolyl, isoxazolyl, thiazolyl, triazolyl, oxazolyl, oxadiazolyl, thiadiazolyl, benzthiazolyl and benzoxazolyl.

The compounds of the present invention have chiral centers and may occur in racemic mixtures or as individual enantiomers or diastereoisomers, with all isomeric forms and mixtures thereof being included within formula I. Thus, the compounds of formula I include (R) and (S) configuration at the chiral centers, marked with an asterisk, and may be depicted as:

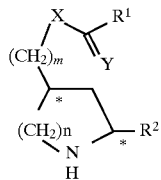

As outlined in the summary of the invention, the compounds of the instant invention are useful for the treatment of a number of NOS implicated diseases. The implication of these diseases is well documented in the literature. For example, with regard to psoriasis, see Ruzicka et al., *J. Invest. Derm.,* 103:397 (1994) or Kolb-Bachofen et al., *Lancet,* 344:139 (1994) or Bull, et al., *J. Invest. Derm.,* 103:435(1994); with regard to uveitis, see Mandia et al., *Invest Opthalmol.,* 35:3673–89 (1994); with regard to type 1 diabetes, see Eisieik & Leijersfam, *Diabetes & Metabolism,* 20:116–22 (1994) or Kroncke et al., *BBRC,* 175:752–8 (1991) or Welsh et al., *Endocrinol.,* 129:3167–73 (1991); with regard to septic shock, see Petros et al., *Lancet,* 338:1557–8 (1991), Thiemermann & Vane, *Eur. J. Pharmacol.,* 211:172–82 (1992), or Evans et al., *Infec. Imm.,* 60:4133–9 (1992), or Schilling et al., *Intensive Care Med.,* 19:227–231 (1993); with regards to pain, see Moore et al., *Brit. J. Pharmacol.,* 102:198–202 (1991), or Moore et al., *Brit. J. Pharmacol.,* 108:296–97 (1992) or Meller et al., *Europ. J. Pharmacol.,* 214:93–6 (1992) or Lee et al., *NeuroReport,* 3:841–4 (1992); with regard to migraine, see Olesen et al., TIPS, 15:149–153 (1994); with regard to rheumatoid arthritis, see Kaurs & Halliwell, *FEBS Letters,* 350:9–12 (1994); with regard to osteoarthritis, see Stadler et al., *J. Immunol.,* 147: 3915–20 (1991) with regard to inflammatory bowel disease, see Miller et al., Lancet, 34:465–66 (1993) or Miller et al., *J. Pharmacol. Exp. Ther.,* 264:11–16 (1993); with regard to asthma, see Hamid et al., Lancet, 342:1510–13 (1993) or Kharitonov, et al., *Lancet,* 343:133–5 (1994); with regard to Immune complex diseases, see Mulligan et al., *Br. J. Pharmacol.,* 107:1159–62 (1992); with regard to multiple sclerosis, see Koprowski et al., *PNAS,* 90:3024–7 (1993); with regard to ischemic brain edema, see Nagafuji et al., *Neurosci.,* 147:159–62 (1992) or Buisson et al., *Br. J. Pharmacol.,* 106:766–67 (1992) or Trifiletti et al., *Europ. J. Pharmacol.,* 218:197–8 (1992); with regard to toxic shock syndrome, see Zembowicz & Vane, *PNAS,* 89:2051–55 (1992); with regard to heart failure, see Winlaw et al., *Lancet,* 344:373–4 (1994); with regard to ulcerative colitis, see Boughton-Smith et al., *Lancet* 342:338–40 (1993); and with regard to atherosclerosis, see White et al., *PNAS,* 91:1044–8 (1994); with regard to glomerulonephritis, see Mühl et al., *Br. J. Pharmcol.,* 112:1–8 (1994); with regard to paget's disease and osteoporosis, see Löwick et al., *J. Clin. Invest.,* 93:1465–72 (1994); with regard to inflammatory sequelae of viral infections, see Koprowski et al., *PNAS,* 90:3024–7 (1993); with regard to retinitis, see Goureau et al., *BBRC,* 186:854–9 (1992); with regard to oxidant induced lung injury, see Berisha et al., *PNAS,* 91:744–9 (1994); with regard to eczema, see Ruzica, et al., *J. Invest. Derm.,* 103:395(1994); with regard to acute allograft rejection, see Devlin, J. et al., *Transplantation,* 58:592–595 (1994); with regard to infection caused by invasive microorganisms which produce NO, see Chen, Y. and Rosazza, J. P. N., *Biochem. Biophys. Res. Comm.,* 203:1251–1258(1994), and with regard to radiocontrast induced renal failure, see Schwaartz, et al., *Am. J. Physiol,* 267:F374–9 (1994).

It will be understood that in the discussion of methods of treatment which follows, references to the compounds of Formula I are meant to also include the pharmaceutically acceptable salts.

The term "pharmaceutically acceptable salts" refers to salts, inorganic or organic. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions contain the active material in admixture with excipients suitable for the manufacture of aqueous suspensions. Such excipients are suspending agents, for example, sodium carboxymethyl-cellulose, methylcellulose, hydroxy-propylmethy-cellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy beans, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention may be synthesized according to the following reaction Schemes and Examples, or modifications thereof, using readily available starting materials, reagents, and conventional synthetic procedures. In these reactions, it is also possible to make use of variants which are themselves known to those of ordinary skill in this art, but are not mentioned in greater detail.

SCHEME 1

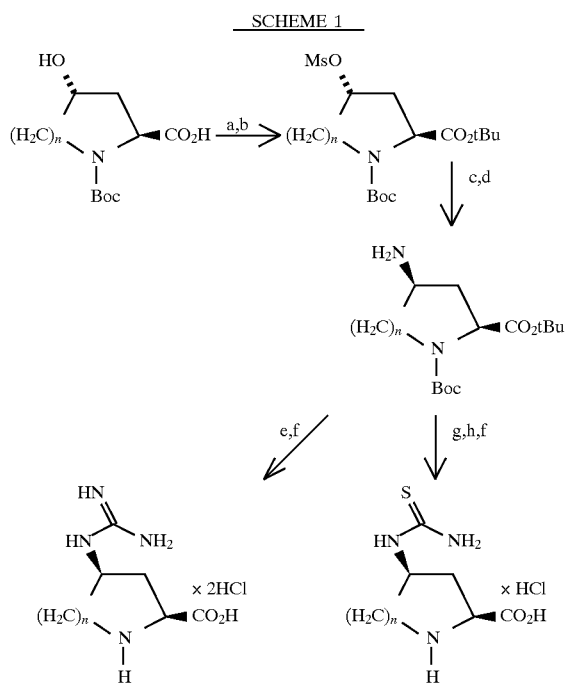

a. CCl$_3$C(=NH)OtBu, BF$_3$.Et$_2$O, CH$_2$Cl$_2$, cyclohexane;
b. MsCl, pyridine, 0° C.;
c. NaN$_3$, DMF, 55° C.;
d. H$_2$, 10% Pd(C), 90% EtOH;
e. BocNHC(=NBoc)SCH$_3$, DMF, 55° C.;
f. 4N HCl/dioxane;
g. Cl$_2$CS, CaCO$_3$;
h. NH$_3$/MeOH.

SCHEME 2

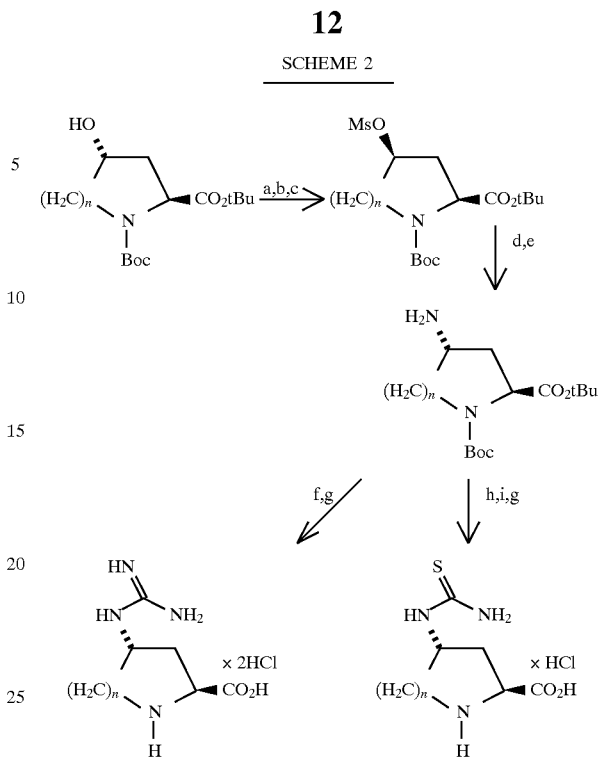

a. 4-nitrobenzoic acid, Ph$_3$P, diethyl azodicarboxylate, C$_6$H$_6$, 80° C.;
b. 0.4N NaOH;
c. MsCl, pyridine, 0° C.;
d. NaN$_3$, DMF, 55° C.;
e. H$_2$, 10% Pd(C), 90% EtOH;
f. BocNHC(=NBoc)SCH$_3$, THF, H$_2$O, 55° C.;
g. 4N HCl/dioxane;
h. Cl$_2$CS, CaCO$_3$;
i. NH$_3$/MeOH.

SCHEME 3

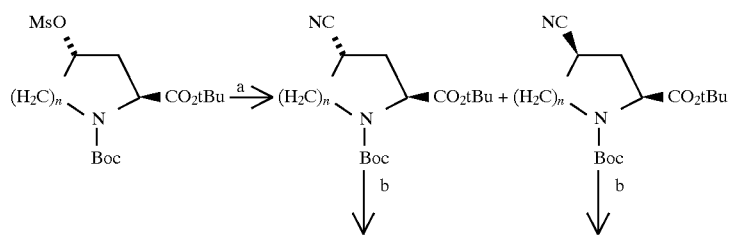

-continued
SCHEME 3

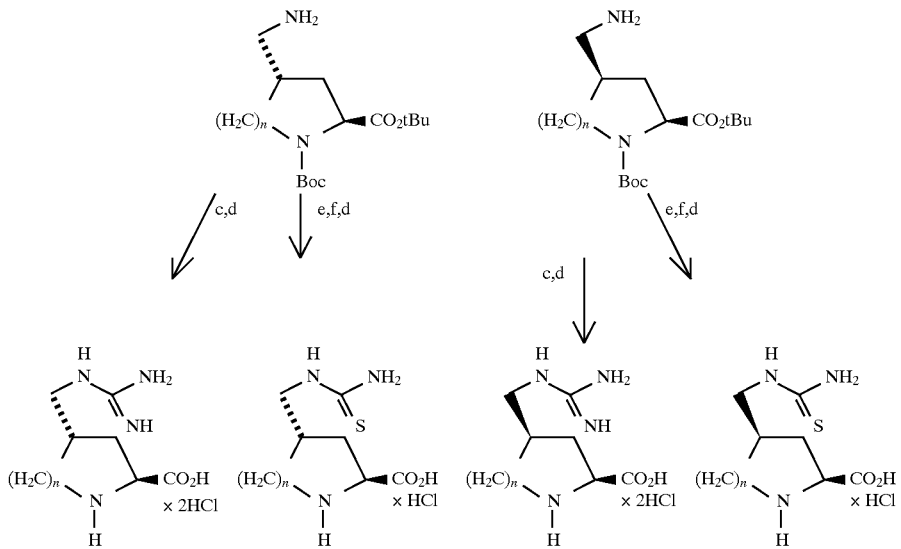

a. NaCN, DMF, 80° C.;
b. $H_2$, 10% Pd(C), 90% EtOH, 450 psi;
c. BocNHC(=NBoc)$SCH_3$, THF, $H_2O$, 55° C.;
d. 4N HCl/dioxane;
e. $Cl_2CS$, $CaCO_3$;
f. $NH_3$/MeOH.

SCHEME 4

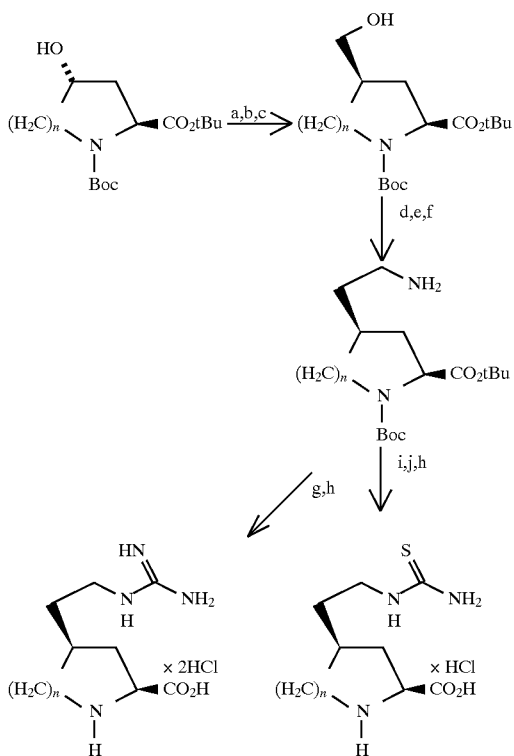

a. tetrapropylammonium perruthenate(VII),
   N-methylmorpholine-N-oxide, 4A sieves, $CH_2Cl_2$;
b. $CH_3PPh_3Br$, NaH, THF;
c. disiamylborane, diglyme, THF, 30% $H_2O_2$, aq. NaOH;
d. MsCl, pyridine, 0° C.;

e. NaCN, DMF, 55° C.;
f. $H_2$, 10% Pd(C), 95% ethanol, 450 psi;
g. BocNH(C=NBoc)$SCH_3$, $Et_3N$, THF, 55° C.;
h. 4N HCl/dioxane;
i. $Cl_2CS$, $CaCO_3$;
4j. $NH_3$/MeOH

SCHEME 5

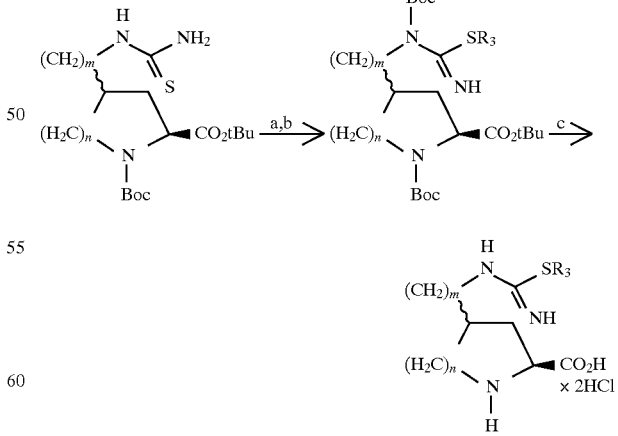

a. $R_3I$, $CH_3CN$;
b. $(Boc)_2O$, dioxane;
c. 4N HCl/dioxane

SCHEME 6

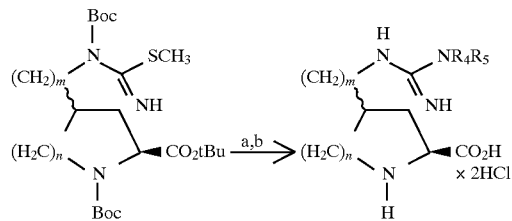

a. R₄R₅NH, MeOH;
b. 4N HCl/dioxane

SCHEME 7

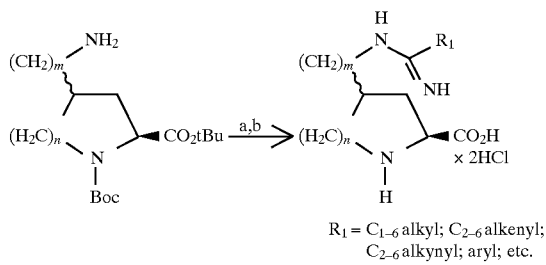

R₁ = C$_{1-6}$ alkyl; C$_{2-6}$ alkenyl;
C$_{2-6}$ alkynyl; aryl; etc.

a. R₁C(=NH)OEt, Et₃N, MeOH;
b. 4N HCl/dioxane

SCHEME 8

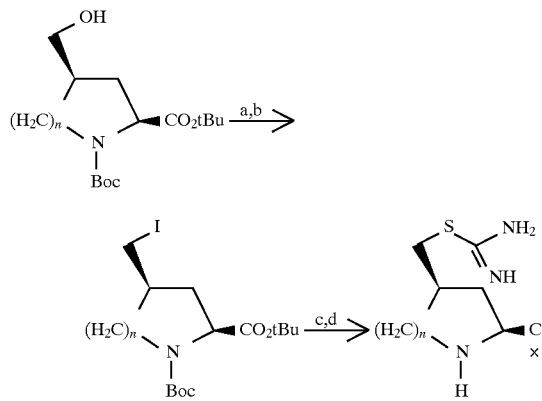

a. MsCl, pyridine, 0° C.;
b. NaI, DMF, 80° C.;
c. thiourea, EtOH, reflux;
d. 4N HCl/dioxane

SCHEME 9

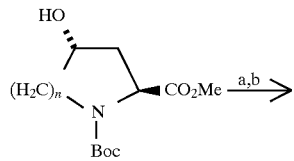

-continued
SCHEME 9

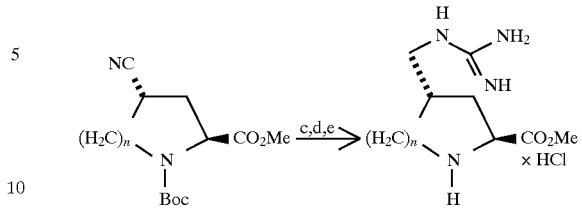

a. MsCl, pyridine, 0° C.;
b. NaCN, DMF, 80° C.;
c. H₂, 10% Pd(C), 90% EtOH, 450 psi;
d. BocNHC(=NBoc)SCH₃, THF, H₂O, 55°;
e. 4N HCl/dioxane The most preferred compounds of the invention are any or all those specifically set forth in these examples. These compounds are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. Unless stated otherwise, all operations were carried out at room or ambient temperature, that is, at a temperature in the range 18°–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 400 MHz using the indicated solvent; conventional abbreviations used for signal shape are: s. singlet; d. doublet; t. triplet; m. multiplet; br. broad; etc.; in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

EXAMPLE 1

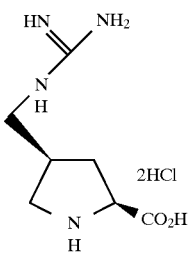

Step A: (4R)-1-(tert-Butyloxycarbonyl)-4-hydroxy-L-Proline tert-Butyl Ester

To a suspension of (4R)-1-(tert-butyloxycarbonyl)-4-hydroxy-L-proline (4.0 g, 17.3 mmol) in dichloromethane (34 mL) was added a solution of tert-butyl trichloroacetimidate (3.8 g, 17.3 mmol) in cyclohexane (68 mL) followed by boron trifluoride-etherate (200 μL, 1.63 mmol). The reaction mixture was stirred overnight at room temperature under a nitrogen atmosphere. A second addition of tert-butyl trichloroacetimidate (3.8 g) and boron trifluoride-etherate (200 μL) was made and the mixture stirred for 5 hours. A third addition was made of each reagent and the mixture stirred for 2 days at room temperature. Insolubles were filtered, the filter washed with a dichloromethane-cyclohexane (1:4) mixture, and the combined filtrate and washings evaporated. The crude mixture was subjected to flash silica gel chromatography eluting with 2% methanol/dichloromethane; yield 2.32 g (47%). Mass spectrum: m/z 232 (M-tBu+1); 400 MHz $^1$H NMR (CDCl$_3$): δ1.42–1.45 (2s, 18H); 2.04 (m, 1H); 2.25 (m, 1H); 3.47 (m, 1H); 3.60 (dd, 1H); 4.27 (m, 1H); 4.45 (m, 1H).

Step B: (4R)-1-(tert-Butyloxycarbonyl)-4-(methanesulfonyloxy)-L-Proline tert-Butyl Ester To a solution of (4R)-1-(tert-butyloxycarbonyl)-4-hydroxy-L-proline tert-butyl ester (573 mg, 1.99 mmol) in pyridine (3.5 mL) cooled to 0° C. was added methanesulfonyl chloride (0.31 mL, 3.99 mmol). The reaction mixture was stirred for 2 hours at ice temperature, diluted with ethyl acetate (30 mL), washed with 1M sodium hydrogencarbonate solution, 1M citric acid, water, dried (Na$_2$SO$_4$), and evaporated. The crude product was purified by flash silica gel chromatography eluting with 1% methanol/dichloromethane; yield 686 mg (94%). 400 MHz $^1$H NMR (CDCl$_3$): δ1.42–1.44 (2s, 18H); 2.20 (m, 1H); 2.60 (m, 1H); 3.02 (s, 3H); 3.68–3.86 (m, 2H); 4.29 (m, 1H); 5.22 (m, 1H).

Step C: (4S)-1-(tert-Butyloxycarbonyl)-4-cyano-L-Proline tert-Butyl Ester

A mixture of (4R)-1-(tert-butyloxycarbonyl)-4-(methanesulfonyloxy)-L-proline tert-butyl ester (680 mg, 1.86 mmol) and sodium cyanide (912 mg, 18.6 mmol) in N,N-dimethylformamide (14 mL) was stirred for 16 hours at 80° C. under a nitrogen atmosphere. The cooled reaction mixture was diluted with ethyl acetate (100 mL), washed with water (2×), saturated brine solution, dried (Na$_2$SO$_4$), and evaporated. The crude product mixture was subjected to flash silica gel chromatography eluting with 20% ethyl acetate/hexane. Fractions containing the TLC less-mobile isomer were combined and evaporated to afford the desired title compound; yield 275 mg (50%). 400 MHz $^1$H NMR (CDCl$_3$): δ1.42–1.48 (4s, 18H); 2.24 (m, 1H); 2.67 (m, 1H); 3.08 (m, 1H); 3.64 (m, 1H); 3.81–3.96 (m, 1H); 4.17–4.28 (m, 1H).

Step D: (4S)-1-(tert-Butyloxycarbonyl)-4-(aminomethyl)-L-Proline tert-Butyl Ester A solution (4S)-1-(tert-butyloxycarbonyl)-4-cyano-L-proline tert-butyl ester (470 mg, 1.59 mmol) in 90% ethanol (22 mL) was hydrogenated in the presence of 10% palladium-on-charcoal (225 mg) at 450 psi for 24 hours. The catalyst was removed by filtration through Celite, the filter washed with ethanol, and the combined filtrate and washings evaporated. Purification was achieved by flash silica gel chromatography eluting with 95:5:0.5 chloroform-methanol-ammonia; yield 284 mg (60%). 400 MHz $^1$H NMR (CD$_3$OD): δ1.41–1.48 (3s, 18H); 1.58 (m, 1H); 2.28 (m, 1H); 2.48 (m, 1H); 2.66 (m, 2H); 3.05 (dd, 1H); 3.71 (dd, 1H); 4.12 (m, 1H).

Step E: (4S)-1-(tert-Butyloxycarbonyl)-4-[N,N'-Bis(tert-Butyl-oxy-carbonyl)guanidinomethyl]-L-Proline tert-Butyl Ester A solution of (4S)-1-(tert-butyloxycarbonyl)-4-(aminomethyl)-L-proline tert-butyl ester (126 mg, 0.419 mmol) and N,N'-bis(tert-butyloxycarbonyl)-S-methylisothiourea (128 mg, 0.440 mmol) in tetrahydrofuran (3.2 mL) and water (60 μL) was heated for 3 hours at 55° C. under a nitrogen atmosphere. The reaction mixture was then evaporated, the residue partitioned between 5% aqueous sodium hydrogencarbonate solution (10 mL) and chloroform (20 mL), and the aqueous layer extracted with chloroform (2×25 mL). The combined extracts were washed with water (10 mL), dried (Na$_2$SO$_4$), and evaporated. The title compound was obtained pure by flash silica gel chromatography eluting with 20% ethyl acetate/hexane; yield 83 mg (37%). Mass spectrum: m/z 543 (M+1); 400 MHz $^1$H NMR (CD$_3$OD): δ1.40–1.52 (4s, 36H); 1.68 (m, 1H); 2.50 (m, 2H); 3.12 (dd, 1H); 3.42 (m, 2H); 3.67 (m, 1H); 4.13 (m, 1H).

Step F: (4S)-4-(Guanidinomethyl)-L-Proline Dihydrochloride (4S)-1-(tert-Butyloxycarbonyl)-4-[N,N'-bis(tert-butyloxycarbonyl)guanidinomethyl]-L-proline tert-butyl ester (81 mg, 0.149 mmol) was treated with 4N HCl in dioxane (1 mL) at room temperature overnight. The reaction mixture was evaporated under diminished pressure, coevaporated several times with diethyl ether and several times with methanol. The product was dried under high vacuum; yield 38.7 mg (100%). Mass spectrum: m/z 187 (M+1); 400 MHz $^1$H NMR (CD$_3$OD): δ1.85 (m, 1H); 2.61–2.80 (m, 2H); 3.13 (dd, 1H); 3.58 (dd, 1H); 4.47 (dd, 1H).

EXAMPLE 2

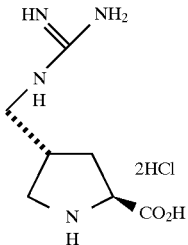

Step A: (4R)-1-(tert-Butyloxycarbonyl)-4-cyano-L-Proline tert-Butyl Ester

A mixture of (4R)-1-(tert-butyloxycarbonyl)-4-(methanesulfonyloxy)-L-proline tert-butyl ester (889 mg, 2.43 mmol) and sodium cyanide (1.19 g, 24.3 mmol) in N,N-dimethylformamide (18 mL) was stirred for 4 days at 80° C. under a nitrogen atmosphere. The cooled reaction mixture was diluted with ethyl acetate (100 mL), washed with water (2×), saturated brine solution, dried (Na$_2$SO$_4$), and evaporated. The crude product mixture was subjected to flash silica gel chromatography eluting initially with 10% ethyl acetate/hexane. Fractions containing the TLC more mobile isomer were combined and evaporated to afford the desired title compound; yield 225 mg (31%).

Step B: (4R)-1-(tert-Butyloxycarbonyl)-4-(aminomethyl)-L-Proline tert-Butyl Ester A solution (4R)-1-(tert-butyloxycarbonyl)-4-cyano-L-proline tert-butyl ester (220 mg, 0.742 mmol) in 90% ethanol (11 mL) was hydrogenated in the presence of 10% palladium-on-charcoal (100 mg) at 450 psi for 18 hours. The catalyst was removed by filtration through Celite, the filter washed with methanol, and the combined filtrate and washings evaporated. Purification was achieved by flash silica gel chromatography eluting with 95:5:0.5 chloroform-methanol-ammonia; yield 164 mg (74%).

Step C: (4R)-1-(tert-Butyloxycarbonyl)-4-[N,N'-Bis(tert-Butyloxycarbonyl)guanidinomethyl]-L-Proline tert-Butyl Ester A solution of (4R)-1-(tert-butyloxycarbonyl)-4-(aminomethyl)-L-proline tert-butyl ester (160 mg, 0.533 mmol) and N,N'-bis(tert-butyloxycarbonyl)-S-methyl-isothiourea (170 mg, 0.586 mmol) in tetrahydrofuran (4.1 mL) and water (80 μL) was heated for 18 hours at 55° C. under a nitrogen atmosphere. The reaction mixture was then evaporated, the residue partitioned between 5% aqueous sodium hydrogencarbonate solution (10 mL) and chloroform (50 mL), and the aqueous layer extracted with chloroform (2×10 mL). The combined extracts were washed with water (25 mL), dried (Na$_2$SO$_4$), and evaporated. The title compound was obtained pure by flash silica gel chromatography eluting with 20% ethyl acetate/hexane; yield 105 mg (36%). Mass spectrum: m/z 543 (M+1); 400 MHz $^1$H NMR (CD$_3$OD): δ1.42–1.53 (4s, 36H); 2.06 (m, 2H); 2.62 (m, 1H); 3.18 (m, 1H); 3.32–3.47 (m, 2H); 3.60 (m, 1H).

Step D: (4R)-4-(Guanidinomethyl)-L-Proline Dihydrochloride (4R)-1-(tert-Butyloxycarbonyl)-4-[N,N'-bis(tert-butyloxy-carbonyl)guanidino-methyl]-L-proline tert-butyl ester (98 mg, 0.181 mmol) was treated with 4N HCl in dioxane (1.5 mL) for 48 hours at room temperature. The reaction mixture was evaporated under diminished pressure, coevaporated several times with diethyl ether and several times with methanol. The product was dried under high vacuum; yield 44 mg (94%). Mass spectrum: m/z 187 (M+1); 400 MHz $^1$H NMR (CD$_3$OD): δ2.19 (m, 1H); 2.43 (m, 1H); 2.68 (m, 1H); 3.11 (dd, 1H); 3.63 (dd, 1H).

EXAMPLE 3

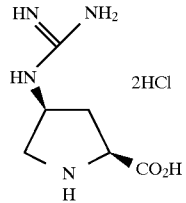

Step A: (4S)-1-(tert-Butyloxycarbonyl)-4-azido-L-Proline tert-Butyl Ester

A mixture of (4R)-1-(tert-butyloxycarbonyl)-4-(methanesulfonyloxy)-L-proline tert-butyl ester (250 mg, 0.684 mmol) and sodium azide (222 mg, 3.42 mmol) in N,N-dimethylformamide (1.5 mL) was stirred for 18 hours at 55° C. under a nitrogen atmosphere. The cooled reaction mixture was evaporated and partitioned between ethyl acetate and water. The organic layer was washed with water, 0.1N hydrochloric acid, water, saturated brine solution, dried (Na$_2$SO$_4$), and evaporated. The crude product mixture was subjected to flash silica gel chromatography eluting with 10% ethyl acetate/hexane. The desired azide was obtained as a colorless oil; yield 194 mg (91%). 400 MHz $^1$H NMR (CDCl$_3$): δ1.42–1.47 (3s, 18H); 2.13 (m, 1H); 2.30–2.47 (m, 1H); 3.37–3.49 (m, 1H); 3.61–3.72 (m, 1H); 4.14 (m, 1H).

Step B: (4S)-1-(tert-Butyloxycarbonyl)-4-amino-L-Proline tert-Butyl Ester

A solution (4S)-1-(tert-butyloxycarbonyl)-4-azido-L-proline tert-butyl ester (185 mg, 0.611 mmol) in 90% ethanol (15 mL) was hydrogenated in the presence of 10% palladium-on-charcoal (40 mg) under a balloon atmosphere of hydrogen gas for one hour. The catalyst was removed by filtration through Celite, the filter washed with methanol, and the combined filtrate and washings evaporated. The title compound was obtained as a colorless oil after drying under high vacuum; yield 145 mg (86%).

Step C: (4S)-1-(tert-Butyloxycarbonyl)-4-[N,N'-Bis(tert-Butyl-oxycarbonyl)guanidino]-L-Proline tert-Butyl Ester A solution of (4R)-1-(tert-butyloxycarbonyl)-4-amino-L-proline tert-butyl ester (134 mg, 0.468 mmol) and N,N'-bis(tert-butyloxycarbonyl)-S-methyl-isothiourea (150 mg, 0.515 mmol) in N,N-dimethylformamide (2 mL) was heated for 15 hours at 55° C. and 2 days at room temperature under a nitrogen atmosphere. The reaction mixture was diluted with diethyl ether, washed with water, dried (Na$_2$SO$_4$), and evaporated. The title compound was obtained pure by flash silica gel chromatography eluting with 10% ethyl acetate/hexane; yield 60.2 mg (24%). Mass spectrum: m/z 529 (M+1); 400 MHz $^1$H NMR (CD$_3$OD): δ1.44–1.52 (4s, 36H); 2.08 (m, 1H); 2.59 (m, 1H); 3.42 (m, 1H); 3.78 (m, 1H); 4.23 (dd, 1H); 4.57 (m, 1H).

Step D: (4S)-4-Guanidino-L-Proline Dihydrochloride (4S)-1-(tert-Butyloxycarbonyl)-4-[N,N'-bis(tert-butyloxycarbonyl)guanidino]-L-proline tert-butyl ester (55 mg, 0.104 mmol) was treated with 4N HCl in dioxane (2 mL) for 48 hours at room temperature. The reaction mixture was evaporated under diminished pressure, coevaporated several times with diethyl ether and several times with methanol. The product was dried under high vacuum; yield 17.5 mg (98%). Mass spectrum: m/z 173 (M+1); 400 MHz $^1$H NMR (CD$_3$OD): δ2.20 (m, 1H); 2.89 (m, 1H); 3.38 (dd, 1H); 3.73 (dd, 1H); 4.43 (m, 1H); 4.51 (t, 1H).

EXAMPLE 4

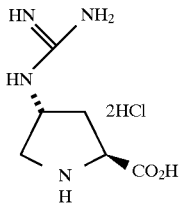

Step A: (4S)-1-(tert-Butyloxycarbonyl)-4-(p-nitrobenzoyloxy)-L-Proline tert-Butyl Ester To a solution of (4R)-1-(tert-butyloxycarbonyl)-4-hydroxy-L-proline (500 mg, 1.74 mmol) in benzene (20 mL) were added triphenylphosphine (548 mg, 2.09 mmol), p-nitrobenzoic acid (349 mg, 2.09 mmol), and diethyl azodicarboxylate (364 mg, 2.09 mmol). The reaction mixture was stirred for 1 hour at 80° C. and then evaporated. Flash silica gel chromatography eluting with 0.5% methanol/dichloromethane gave the desired product in 77% yield (581 mg). 400 MHz $^1$H NMR (CDCl$_3$): δ1.38–1.47 (3s, 18H); 2.37 (m, 1H); 2.49–2.61 (m, 1H); 5.53 (m, 1H); 8.16–8.27 (m, 4H, Ar).

Step B: (4S)-1-(tert-Butyloxycarbonyl)-4-hydroxy-L-Proline tert-Butyl Ester

A solution of (4S)-1-(tert-butyloxycarbonyl)-4-(p-nitrobenzoyloxy)-L-proline tert-butyl ester (575 mg, 1.32 mmol) in ethanol (13 mL) was treated with 0.4N sodium hydroxide (4.3 mL, 1.72 mmol) for 18 hours at room temperature. The solution was neutralized with several drops of glacial acetic acid, diluted with ethyl acetate (100 mL), washed with water (2×), saturated brine solution, dried (Na$_2$SO$_4$), and evaporated. The residue was subjected to flash silica gel chromatography eluting with 5% acetone/dichloromethane. The title compound (313 mg) was obtained contaminated with some p-nitrobenzoic acid and used without further purification in the next step.

Step C: (4S)-1-(tert-Butyloxycarbonyl)-4-(methanesulfonyloxy)-L-Proline tert-Butyl Ester To a solution of (4S)-1-(tert-butyloxycarbonyl)-4-hydroxy-L-proline tert-butyl ester (313 mg, 1.09 mmol) in pyridine (2.0 mL) cooled to 0° C. was added methanesulfonyl chloride (0.17 mL, 2.18 mmol). The reaction mixture was allowed to reach room temperature, and after 2 hours was diluted with ethyl acetate (100 mL), washed with saturated sodium hydrogencarbonate solution, 1 M citric acid, water, dried (Na$_2$SO$_4$), and evaporated. The crude product was purified by flash silica gel chromatography eluting with 15% acetone/hexane; yield 251 mg (52% over 2 steps). 400 MHz $^1$H NMR (CDCl$_3$): δ1.42–1.48 (3s, 18H); 2.38–2.50 (m, 2H); 2.99 (2s, 3H); 3.69–3.79 (m, 2H); 5.22 (m, 1H).

Step D: (4R)-1-(tert-Butyloxycarbonyl)-4-azido-L-Proline tert-Butyl Ester

A mixture of (4S)-1-(tert-butyloxycarbonyl)-4-(methanesulfonyloxy)-L-proline tert-butyl ester (250 mg, 0.684 mmol) and sodium azide (222 mg, 3.42 mmol) in N,N-dimethylformamide (1.5 mL) was stirred for 18 hours at 55° C. under a nitrogen atmosphere. The cooled reaction mixture was evaporated and partitioned between diluted ethyl acetate and water. The organic layer was washed with water, 0.1N hydrochloric acid, water, saturated brine solution, dried (Na$_2$SO$_4$), and evaporated. The crude product mixture was subjected to flash silica gel chromatography eluting with 10% ethyl acetate/hexane. The desired azide was obtained as a colorless oil; yield 196 mg (92%). 400 MHz $^1$H NMR (CDCl$_3$): δ1.42–1.45 (3s, 18H); 2.11 (m, 1H); 2.22–2.36 (m, 1H); 3.68 (m, 1H); 4.12 (m, 1H).

Step E: (4R)-1-(tert-Butyloxycarbonyl)-4-amino-L-Proline tert-Butyl Ester

A solution (4R)-1-(tert-butyloxycarbonyl)-4-azido-L-proline tert-butyl ester (191 mg, 0.611 mmol) in 90% ethanol (15 mL) was hydrogenated in the presence of 10% palladium-on-charcoal (40 mg) under a balloon atmosphere of hydrogen gas for one hour. The catalyst was removed by filtration through Celite, the filter washed with methanol, and the combined filtrate and washings evaporated. The title compound was obtained as a colorless oil after drying under high vacuum; yield 177 mg.

Step F: (4R)-1-(tert-Butyloxycarbonyl)-4-[N,N'-Bis(tert-Butyloxycarbonyl)guanidino]-L-Proline tert-Butyl Ester A solution of (4R)-1-(tert-butyloxycarbonyl)-4-amino-L-proline tert-butyl ester (172 mg, 0.600 mmol) and N,N'-bis(tert-butyloxycarbonyl)-S-methyl-isothiourea (192 mg, 0.661 mmol) in tetrahydrofuran (3.5 mL) and water (70 μL) was heated for 18 hours at 55° C. and 1 day at room temperature under a nitrogen atmosphere. The reaction mixture was evaporated, and the title compound was obtained pure by flash silica gel chromatography eluting with 15% ethyl acetate/hexane; yield 114 mg (36%). Mass spectrum: m/z 529 (M+1); 400 MHz $^1$H NMR (CD$_3$OD): δ1.44–1.52 (36H); 2.20–2.39 (m, 2H); 3.39 (m, 1H); 3.74 (dd, 1H); 4.13 (m, 1H).

Step G: (4R)-4-Guanidino-L-Proline Dihydrochloride (4R)-1-(tert-Butyloxycarbonyl)-4-[N,N'-bis(tert-butyloxycarbonyl)guanidino]-L-proline tert-butyl ester (114 mg, 0.216 mmol) was treated with 4N HCl in dioxane (2 mL) for 48 hours at room temperature. The reaction mixture was evaporated under diminished pressure, coevaporated several times with diethyl ether and several times with methanol. The product was dried under high vacuum, and a quantitative yield of the title compound was obtained. Mass spectrum: m/z 173 (M+1); 400 MHz $^1$H NMR (CD$_3$OD): δ2.49 (m, 1H); 2.58 (m, 1H); 3.40 (dd, 1H); 3.77 (dd, 1H); 4.42 (m, 1H); 4.66 (t, 1H).

EXAMPLE 5

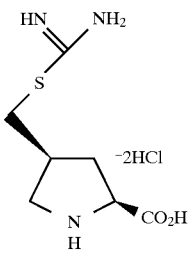

Step A: 1-(tert-Butyloxycarbonyl)-4-oxo-L-Proline tert-Butyl Ester

To a solution of (4R)-1-(tert-butyloxycarbonyl)-4-hydroxy-L-proline (1.0 g, 3.48 mmol) in dichloromethane (3 mL) was added 4-methylmorpholine N-oxide (612 mg, 5.22 mmol) followed by 4 Å powdered molecular sieves (1.74 g) and tetrapropylammonium perruthenate(VII) (TPAP) (61 mg, 0.174 mmol). After stirring for 1 hour at room temperature, an additional 30 mg of TPAP was added, and the reaction was continued for 2 hours. The reaction mixture was applied to a column of silica gel (packed in 20% ethyl acetate/hexane). Elution with the same mobile phase afforded pure ketone as a white crystalline solid; yield 610 mg (61%). 400 MHz $^1$HNMR (CDCl$_3$): δ1.43 (s, 9H); 1.47 (s, 9H); 2.50 (dd, 1H); 2.89 (m, 1H); 3.82–3.93 (m, 2H); 4.60 (dd, 1H).

Step B: 1-(tert-Butyloxycarbonyl)-4-C-methylene-L-Proline tert-Butyl Ester

To an oven-dried 2-necked round-bottomed flask was added sodium hydride (80% oil dispersion) (497 mg, 16.56 mmol) followed by dry tetrahydrofuran (42 mL) and methyltriphenyl-phosphonium bromide (5.92 g, 16.56 mmol). The suspension was stirred for 4 hours at 50° C., at which time a solution of 1-(tert-butyloxycarbonyl)-4-oxo-L-proline tert-butyl ester (1.18 g, 4.14 mmol) in THF (10 mL) was added dropwise with stirring over 30 minutes. The reaction mixture was stirred for 2 hours at 50° C., cooled, filtered, and evaporated. The residue was taken up in ethyl acetate (100 mL), washed with N hydrochloric acid (2×), water (2×), saturated brine solution, dried (Na$_2$SO$_4$), and evaporated. The crude product was subjected to flash silica gel chromatography eluting with 15% diethyl ether/hexane. The title compound was obtained as a colorless oil; yield 519 mg (43%). 400 MHz $^1$HNMR (CDCl$_3$): δ1.42–1.47 (3s, 18H); 2.54 (m, 1H); 2.92 (m, 1H); 4.03 (m, 2H); 4.23–4.38 (m, 1H); 4.98 (m, 2H).

Step C: (4S)-1-(tert-Butyloxycarbonyl)-4-(Hydroxymethyl)-L-Proline tert-Butyl Ester To an oven-dried 100-mL 2-necked round-bottomed flask was added a solution of 1-(tert-butyloxycarbonyl)-4-C-methylene-L-proline tert-butyl ester (519 mg, 1.83 mmol) in 2-methoxyethyl ether (diglyme) (5 mL) followed at 0° C. by a solution of disiamylborane (12.8 ML of a 0.5M solution in tetrahydrofuran, 6.41 mmol) in diglyme (15 mL). After stirring for 15 minutes at 0° C., the cooling bath was removed, and the mixture was allowed to warm up for 15 minutes. The reaction was then quenched by the careful addition of water (25 mL). The reaction mixture was again cooled to 0° C., and the pH was adjusted to 8 with 3N sodium hydroxide. 30% Hydrogen peroxide (4 mL) was added dropwise slowly with the temperature maintained at 0° C. for 10 minutes. The cooling bath was removed for 10 minutes, and an additional 1.3 mL of 30% hydrogen peroxide was added, while maintaining the pH at 8 by addition of 3N sodium hydroxide. The pH was then adjusted to ~6 by the addition of glacial acetic acid. The mixture was partitioned between diethyl ether (100 mL) and water (50 mL), and the aqueous layer extracted with ether. The combined ethereal layers were washed with water, dried (MgSO₄), and evaporated. Flash silica gel chromatography eluting with 20% acetone/hexane afforded the title compound as a colorless oil; yield 376 mg (68%).

Step D: (4S)-1-(tert-Butyloxycarbonyl)-4-(Methanesulfonyl-oxymethyl)-L-Proline tert-Butyl Ester To a solution of (4S)-1-(tert-butyloxycarbonyl)-4-hydroxymethyl-L-proline tert-butyl ester (364 mg, 1.21 mmol) in pyridine (2 mL) cooled to 0° C. was added methanesulfonyl chloride (0.19 mL, 2.42 mmol). The reaction mixture was stirred for 2 hours at ice temperature, diluted with ethyl acetate (100 mL), washed with 1M sodium hydrogencarbonate solution, 1M citric acid, water, saturated brine solution, dried (Na₂SO₄), and evaporated. The crude product was purified by flash silica gel chromatography eluting with 20% acetone/hexane; yield 437 mg (95%).

Step E: (4S)-1-(tert-Butyloxycarbonyl)-4-(iodomethyl)-L-Prolinetert-Butyl Ester

To a solution of (4S)-1-(tert-butyloxycarbonyl)-4-(methanesulfonyloxymethyl)-L-proline tert-butyl ester (216 mg, 0.569 mmol) in N,N-dimethylformamide (4.5 mL) was added sodium iodide (256 mg, 1.71 mmol). The reaction mixture was stirred for 18 hours at 80° C., cooled, diluted with ethyl acetate (100 mL), washed with water (2×), dried (Na₂SO₄), and evaporated. The title compound was obtained pure subsequent to flash silica gel chromatography eluting with 10% ethyl acetate/hexane; yield 182 mg (78%). Mass spectrum: m/z 411 (M).

Step F: (4S)-1-(tert-Butyloxycarbonyl)-4-[(isothioureido)methyl]-L-Prolinetert-Butyl Ester A solution of (4S)-1-(tert-butyloxycarbonyl)-4-(iodomethyl)-L-proline tert-butyl ester (90 mg, 0.219 mmol) and thiourea (50 mg, 0.656 mmol) in ethanol (2 mL) was heated at reflux temperature for 18 hours. The cooled reaction mixture was evaporated, taken up in dichloromethane, washed with saturated sodium hydrogencarbonate solution (2×), water (2×), dried (Na₂SO₄), and evaporated. Flash silica gel chromatography eluting with 40:10:1 chloroform-methanol-water afforded the title compound; yield 25.1 mg (32%). Mass spectrum: m/z 360 (M+1); 400 MHz ¹H NMR (CD₃OD): δ1.43–1.48 (4s, 18H); 1.72 (m, 1H); 3.72 (m, 1H); 4.15 (m, 1H).

Step G: (4S)-4-[(Isothioureido)methyl]-L-Proline Dihydrochloride (4S)-1-(tert-Butyloxycarbonyl)-4-[(isothioureido)methyl]-L-proline tert-butyl ester (25 mg, 0.070 mmol) was treated with 4N HCl in dioxane (1 mL) for 18 hours at room temperature. The reaction mixture was evaporated under diminished pressure, coevaporated several times with diethyl ether, several times with methanol, and finally ether. The product was dried under high vacuum to afford the title compound; yield 14 mg (73%). Mass spectrum: m/z 203 (M); 400 MHz ¹H NMR (CD₃OD): δ1.92 (m, 1H); 3.18 (m, 1H); 4.48 (m, 1H).

EXAMPLE 6

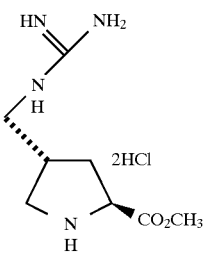

Step A: (4R)-1-(tert-Butyloxycarbonyl)-4-(methanesulfonyloxy)-L-Proline Methyl Ester To a solution of (4R)-1-(tert-butyloxycarbonyl)-4-hydroxy-L-proline methyl ester (2.0 g, 8.15 mmol) in pyridine (15 mL) cooled to 0° C. was added methanesulfonyl chloride (1.3 mL, 16.8 mmol). The reaction mixture was stirred for 2 hours at ice temperature, diluted with ethyl acetate (30 mL), washed with 1M sodium hydrogencarbonate solution, 1M citric acid, saturated brine solution, dried (Na₂SO₄), and evaporated. The crude product was purified by flash silica gel chromatography eluting with 25% acetone/hexane; yield 2.36 g (89%). 400 MHz ¹H NMR (CDCl₃): δ1.40–1.44 (2s, 9H), 3.03 (s, 3H), 3.72 (2s, 3H), 4.37–4.47 (m, 1H), 5.23 (m, 1H).

Step B: (4R)-1-(tert-Butyloxycarbonyl)-4-cyano-L-Proline Methyl Ester

A mixture of (4R)-1-(tert-butyloxycarbonyl)-4-(methanesulfonyloxy)-L-proline methyl ester (2.31 g, 7.14 mmol) and sodium cyanide (3.5 g, 71.4 mmol) in dry dimethylsulfoxide (46 mL) was stirred for 24 hours at 55° C. under a nitrogen atmosphere. The cooled reaction mixture was diluted with ethyl acetate, washed with water (2×), saturated brine solution, dried (MgSO₄), and evaporated. The crude product mixture was subjected to flash silica gel chromatography eluting with 15% acetone/hexane. Fractions containing the desired nitrile were combined and evaporated to afford a colorless oil; yield 205 mg (11%).

Step C: (4R)-1-(tert-Butyloxycarbonyl)-4-(aminomethyl)-L-Proline Methyl Ester

A solution (4R)-1-(tert-butyloxycarbonyl)-4-cyano-L-proline methyl ester (204 mg, 0.802 mmol) in 90% ethanol (12 mL) was hydrogenated in the presence of 10% palladium-on-charcoal (60 mg) at 450 psi for 24 hours. The catalyst was removed by filtration through Celite, the filter washed with ethanol, and the combined filtrate and washings evaporated. Purification was achieved by flash silica gel chromatography eluting with 95:5:0.5 chloroform-methanol-ammonia; yield 66 mg (32%).

Step D: (4R)-1-(tert-Butyloxycarbonyl)-4-[N,N'-Bis(tert-Butyl-oxycarbonyl)guanidinomethyl]-L-Proline Methyl Ester A solution of (4R)-1-(tert-butyloxycarbonyl)-4-(aminomethyl)-L-proline methyl ester (64 mg, 0.248 mmol) and N,N'-bis(tert-butyloxycarbonyl)-S-methyl-isothiourea (79 mg, 0.272 mmol) in tetrahydrofuran (3.0 mL) and water (60 μL) was heated for 3 hours at 55° C. and for 18 hours at room temperature under a nitrogen atmosphere. The reaction mixture was then evaporated, and the residue applied to a column of silica gel. Elution with 20% ethyl acetate/hexane gave the title compound; yield 14.3 mg (12%). Mass spectrum: m/z 501 (M+1); 400 MHz ¹H NMR (CD₃OD): δ1.40–1.53 (4s, 27H); 2.08 (m, 1H); 2.60 (m, 1H); 3.19 (m, 1H); 3.61 (m, 1H); 3.72 (2s, 3H); 4.35 (m, 1H).

Step E: (4R)-4-(Guanidinomethyl)-L-Proline Methyl Ester Dihydrochloride (4R)-1-(tert-Butyloxycarbonyl)-4-[N,N'-bis(tert-butyloxy-carbonyl)guanidinomethyl]-L-proline methyl ester (14 mg, 0.028 mmol) was treated with 4N HCl in dioxane (1 mL) at room temperature overnight. The reaction mixture was evaporated under diminished pressure, coevaporated several times with diethyl ether and several times with methanol. The product was dried under high vacuum; yield 7.6 mg (100%). Mass spectrum: m/z 201 (M+1); 400 MHz $^1$H NMR (CD$_3$OD): δ2.19 (m, 1H); 2.42 (m, 1H); 2.68 (m, 1H); 3.11 (dd, 1H); 3.64 (dd, 1H); 3.87 (s, 3H); 4.60 (dd, 1H).

Isolation and Purification of Nitric Oxide Synthases

Methods demonstrating the isolation and purification of all three isoforms of NOS have been published and reviewed in U. Forstermann, J. S. Pollock, W. R. Tracey, M. Nakane in *Methods in Enzymology*, Vol. 233, L. Packer, ed., Academic Press, NY, 1994, Ch. 26, pp. 258–264. Cloned and expressed NOS has also been demonstrated and reviewed in C. J Lowenstein and S. H. Snyder in Methods in *Enzymology, Vol.* 233, L. Packer, ed., Academic Press, NY, 1994, Ch. 26, pp. 264–269.

Assay Protocol for NOS activity

Various assays for NOS activity have been reported in the literature and are reviewed in the following: M. E. Murphy and E. Noack in *Methods in Enzymology*, Vol. 233, L. Packer, ed., Academic Press, NY, 1994, Ch. 26, pp. 240–250 and J. M. Hevel and M. A. Marletta in *Methods in Enzymology*, Vol. 233, L. Packer, ed., Academic Press, NY, 1994, Ch. 26, pp. 250–258. Details for the assay protocols to measure NOS activity are as follows:

NOS activity is measured as the formation of L-[2,3,4,5-$^3$H]Citrulline from L-[2,3,4,5-$^3$H]Arginine. The incubation buffer (100 μL) contained; 100 mM TES, pH 7.5, 5 μM FAD, 5 μM FMN, 10 μM BH$_4$, 0.5 mM NADPH, 0.5 mM DTT, 0.5 mg/mL BSA, 2 mM CaCl2, 10 μg/mL calmodulin (bovine), 1 μM L-Arg, 0.2 μCi L-[2,3,4,5-$^3$H]Arg, and the inhibitor in aqueous DMSO (max. 5%). The reaction is initiated by addition of enzyme. Incubations are performed at room temperature for 30 minutes and stopped by the addition of an equal volume of quenching buffer consisting of 200 mM sodium citrate, pH 2.2, 0.02% sodium azide. Reaction products are separated by passing through a cation exchange resin and quantitated as cpm by scintillation counting. Percent inhibition is calculated relative to enzyme incubated without inhibitor according to: % inhibition=100× (cpm L-[2,3,4,5-$^3$H]Cit with inhibitor/cpm L-[2,3,4,5-$^3$H] Cit without inhibitor).

Illustrative of the utility of the compounds of Formula I is the ability of such compounds to inhibit NO synthase as shown in Table 1 and as measured by the assay described above:

TABLE 1

Inhibition of Human Inducible Nitric Oxide Synthase by Aza Heterocycles

| Cmpd No. | Name | IC$_{50}$ (μM) |
|---|---|---|
| 1 | (4R)-4-(guanidinomethyl)-L-proline dihydrochloride | 7.1 |
| 2. | (4R)-4-(guanidinomethyl)-L-proline dihydrochloride | 3.5 |
| 3. | (4S)-4-guanidino-L-proline dihydrochloride | 2.7 |
| 5. | (4S)-4-(isothioureidomethyl)-L-proline dihydrochloride | 111 |

TABLE 1-continued

Inhibition of Human Inducible Nitric Oxide Synthase by Aza Heterocycles

| Cmpd No. | Name | IC$_{50}$ (μM) |
|---|---|---|
| 6 | (4R)-4-(guanidinomethyl)-L-proline methyl ester dihydrochloride | 11 |

What is claimed is:

1. A method for inhibiting the activity of nitric oxide synthases comprising administering to a subject suffering from a nitric oxide synthase mediated disease, a non-toxic therapeutically effective amount of a compound of Formula (I):

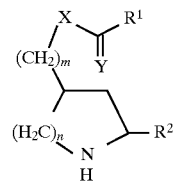

or a pharmaceutically acceptable salt thereof wherein:
m is 0, 1, 2 or 3;
n is 1 or 2;
R$_1$ is
  (1) —SR$_3$;
  (2) —N(R$_4$)(R$_5$);
  (3) hydrogen,
  (4) C$_{1-6}$alkyl,
  (5) C$_{2-6}$alkenyl,
  (6) C$_{2-6}$alkynyl,
  (7) R$_6$-A,
  (8) 3- to 10-membered monocyclic ring which optionally contains 1 or 2 heteroatoms selected from S, O, and N, each of (4) to (8) being optionally mono- or di- substituted, the substituents being independently selected from
    (a) R$_8$, and
    (b) C$_{1-6}$alkyl, with the proviso that for items (4), (5) and (6) the substituent is other than C$_{1-6}$alkyl;
R$_2$ is —COOR$_9$;
R$_3$ is R$_7$ optionally substituted with R$_8$,
R$_4$ and R$_5$ are each independently selected from the group consisting of
  (1) hydrogen,
  (2) hydroxy,
  (3) amino,
  (4) cyano,
  (5) nitro,
  (6) trifluoromethyl,
  (7) C$_{1-6}$alkyl,
  (8) C$_{2-6}$alkenyl,
  (9) C$_{2-6}$alkynyl,
  (10) R$_6$-A,
  (11) 3- to 10-membered monocyclic ring which optionally contains 1 or 2 heteroatoms selected from S, O, and N,
  (12) R$_7$—C$_{3-6}$cycloalkyl,
  each of (7) to (12) being optionally mono- or di-substituted, with substituents being independently selected from
    (a) R8, and (b) $C_{1-6}$alkyl, with the proviso that (7), (8) and (9) must each be other than $C_{1-6}$alkyl, $R_4$, $R_5$ together with the nitrogen to which they are attached join to form a 4- to 6-membered saturated or unsaturated ring containing 1 or 2 heteroatoms selected from S, O and N;

R6 is
(1) a bond, or
(2) $R_7$, $R_7$ is
(1) $C_{1-6}$alkyl,
(2) $C_{2-6}$alkenyl, or
(3) $C_{2-6}$alkynyl, $R_8$ is
(1) hydroxy,
(2) $C_{1-6}$alkylcarbonyl,
(3) $C_{1-6}$alkoxy,
(4) amino,
(5) mono- and di-$C_{1-6}$alkylamino,
(6) carboxyl,
(7) $C_{1-6}$alkylthio,
(8) $C_{1-6}$alkyl-$S(O)_k$—, where k is 1 or 2,
(9) $C_{1-6}$alkyoxycarbonyl,
(10) halo selected from fluoro, chloro, bromo, and iodo, and
(11) $CF_3$ $R_9$ is H, $C_{1-6}$alkyl or phenyl-$C_{0-3}$alkyl, A is
(1) phenyl
(2) naphthyl, or
(3) heteroaryl selected from the group consisting of
 (a) pyridyl,
 (b) pyrrolyl,
 (c) furanyl,
 (d) isothiazolyl,
 (e) imidazolyl,
 (f) benzimidazolyl,
 (g) tetrazolyl,
 (h) pyrazinyl,
 (i) pyrimidyl,
 (j) quinolyl,
 (k) isoquinolyl,
 (l) benzofuranyl,
 (m) isobenzofuryl,
 (n) benzothienyl,
 (o) pyrazolyl,
 (p) indolyl,
 (q) isoindolyl,
 (r) purinyl,
 (s) carbazolyl,
 (t) isoxazolyl,
 (u) thiazolyl,
 (v) triazolyl
 (w) oxazolyl,
 (x) oxadiazolyl,
 (y) thiadiazolyl
 (z) benzthiazolyl,
 (a') benzoxazolyl, and
 (b') thienyl, X is S or NH,
Y is selected from the group consisting of
(1) O,
(2) S,
(3) —NH, and
(4) —N—$R_7$, wherein $R_7$ is optionally mono- or di- substituted, the substituents being independently selected from $R_8$;

with the proviso that at least two of the groups X, Y and $R_1$ are an amino or substituted amino group.

2. A pharmaceutical composition for treating a nitric oxide synthase mediated disease comprising a pharmaceutical carrier and a non-toxic effective amount of a compound of Formula (I).

3. A method according to claim 1 wherein said compound of Formula (I) is selected from the group consisting of:
 (a) (4R)-4-guanidinomethyl-L-proline dihydrochloride;
 (b) (4S)-4-guanidinomethyl-L-proline dihydrochloride;
 (c) (4R)-4-guanidino-L-proline dihydrochloride;
 (d) (4S)-4-guanidino-L-proline dihydrochloride;
 (e) (4R)-4-guanidinomethyl-L-proline methyl ester dihydrochloride; and
 (f) (4R)-4-(isothioureidomethyl)-L-proline dihydrochloride.

4. A pharmaceutical composition according to claim 3 wherein said compound of Formula (I) is selected from
 (a) (4R)-4-guanidinomethyl-L-proline dihydrochloride;
 (b) (4S)-4-guanidinomethyl-L-proline dihydrochloride;
 (c) (4R)-4-guanidino-L-proline dihydrochloride;
 (d) (4S)-4-guanidino-L-proline dihydrochloride;
 (e) (4R)-4-guanidinomethyl-L-proline methyl ester dihydrochloride; and
 (f) (4R)-4-(isothioureidomethyl)-L-proline dihydrochloride.

5. A compound having the Formula (I):

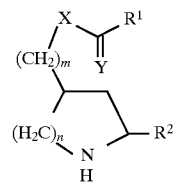

or a pharmaceutically acceptable salt thereof wherein:
m is 0, 1, 2 or 3;
n is 1 or 2;
$R_1$ is
 (1) —$SR_3$;
 (2) —$N(R_4)(R_5)$;
 (3) hydrogen,
 (4) $C_{1-6}$alkyl,
 (5) $C_{2-6}$alkenyl,
 (6) $C_{2-6}$alkynyl,
 (7) $R_6$-A,
 (8) 3- to 10-membered monocyclic ring which optionally contains 1 or 2 heteroatoms selected from S, O, and N, each of (4) to (8) being optionally mono- or di- substituted, the substituents being independently selected from
  (a) $R_8$, and
  (b) $C_{1-6}$alkyl, with the proviso that for items (4), (5) and (6) the substituent is other than $C_{1-6}$alkyl;
$R_2$ is —$COOR_9$;
$R_3$ is $R_7$ optionally substituted with $R_8$,
$R_4$ and $R_5$ are each independently selected from the group consisting of
 (1) hydrogen,
 (2) hydroxy,
 (3) amino,
 (4) cyano,
 (5) nitro, (6) trifluoromethyl,
(7) $C_{1-6}$alkyl,
(8) $C_{2-6}$alkenyl,
(9) $C_{2-6}$alkynyl,
(10) $R_6$-A,
(11) 3- to 10-membered monocyclic ring which optionally contains 1 or 2 heteroatoms selected from S, O, and N,
(12) $R_7$—$C_{3-6}$cycloalkyl, each of (7) to (12) being optionally mono- or di- substituted, with substituents being independently selected from
  (a) R8, and
  (b) $C_{1-6}$alkyl, with the proviso that (7), (8) and (9) must each be other than $C_{1-6}$alkyl, $R_4$, $R_5$ together with the nitrogen to which they are attached join to form a 4- to 6-membered saturated or unsaturated ring containing 1 or 2 heteroatoms selected from S, O and N;

R6 is
  (1) a bond, or
  (2) $R_7$, $R_7$ is
  (1) $C_{1-6}$alkyl,
  (2) $C_{2-6}$alkenyl, or
  (3) $C_{2-6}$alkynyl, $R_8$ is
  (1) hydroxy,
  (2) $C_{1-6}$alkylcarbonyl,
  (3) $C_{1-6}$alkoxy,
  (4) amino,
  (5) mono- and di-$C_{1-6}$alkylamino,
  (6) carboxyl,
  (7) $C_{1-6}$alkylthio,
  (8) $C_{1-6}$alkyl-S(O)$_k$—, where k is 1 or 2,
  (9) $C_{1-6}$alkyoxycarbonyl,
  (10) halo selected from fluoro, chloro, bromo, and iodo, and
  (11) $CF_3$ $R_9$ is H, $C_{1-6}$alkyl or phenyl-$C_{0-3}$alkyl, A is
  (1) phenyl
  (2) naphthyl, or
  (3) heteroaryl selected from the group consisting of
    (a) pyridyl,
    (b) pyrrolyl,
    (c) furanyl,
    (d) isothiazolyl,
    (e) imidazolyl,
    (f) benzimidazolyl,
    (g) tetrazolyl,
    (h) pyrazinyl,
    (i) pyrimidyl,
    (j) quinolyl,
    (k) isoquinolyl,
    (l) benzofuranyl,
    (m) isobenzofuryl,
    (n) benzothienyl,
    (o) pyrazolyl,
    (p) indolyl,
    (q) isoindolyl,
    (r) purinyl,
    (s) carbazolyl,
    (t) isoxazolyl,
    (u) thiazolyl,
    (v) triazolyl
    (w) oxazolyl,
    (x) oxadiazolyl,
    (y) thiadiazolyl
    (z) benzthiazolyl,
    (a') benzoxazolyl, and
    (b') thienyl, X is S or NH, Y is selected from the group consisting of
  (1) O,
  (2) S,
  (3) —NH, and
  (4) —N—$R_7$, wherein $R_7$ is optionally mono- or di-substituted, the substituents being independently selected from $R_8$;

with the proviso that at least two of the groups X, Y and $R_1$ are an amino or substituted amino group, and with the further proviso that when n is 1, X and Y are each -NH, and $R_1$ is —$NH_2$, m is other than 0 or 1.

6. A compound of claim 5 wherein
$R_1$ is —N($R_4$)($R_5$)
Y is selected from the group consisting of
  (1) —NH, or
  (2) —N—$R_7$, and
$R_4$, $R_5$, $R_7$ are as defined in claim 5.

7. A compound of claim 5 wherein
m is 0 or 1;
n is 1;
$R_1$ is —N($R_4$)($R_5$),
$R_2$ is —COOR$_9$;
$R_9$ is H or $C_{1-3}$alkyl;
X is NH;
Y is NH; and
$R_4$ and $R_5$ are as defined above.

* * * * *